(12) United States Patent
Vardanyan et al.

(10) Patent No.: US 11,440,885 B2
(45) Date of Patent: *Sep. 13, 2022

(54) SUBSTITUTED 1-ARYLALKYL-4-ACYLAMINOPIPERIDINE COMPOUNDS AND METHODS OF PRODUCING AND USING THE SAME

(71) Applicant: Arizona Board of Regents on Behalf of the University of Arizona, Tucson, AZ (US)

(72) Inventors: Ruben S. Vardanyan, Tucson, AZ (US); Victor J. Hruby, Tucson, AZ (US)

(73) Assignee: ARIZONA BOARD OF REGENTS ON BEHALF OF THE UNIVERISTY OF ARIZONA, Tucson, AZ (US)

( * ) Notice: Subject to any disclaimer, the term of this patent is extended or adjusted under 35 U.S.C. 154(b) by 64 days.

This patent is subject to a terminal disclaimer.

(21) Appl. No.: 16/829,299

(22) Filed: Mar. 25, 2020

(65) Prior Publication Data

US 2020/0222380 A1 Jul. 16, 2020

Related U.S. Application Data

(60) Continuation of application No. 15/756,014, filed as application No. PCT/US2016/030649 on May 4, 2016, now abandoned, which is a continuation-in-part of application No. 14/834,185, filed on Aug. 24, 2015, now Pat. No. 9,765,027, application No. 16/829,299, which is a continuation-in-part of application No. 16/236,981, filed on Dec. 31, 2018, now Pat. No. 10,617,681, which is a division of application No. 15/709,394, filed on Sep. 19, 2017, now abandoned, which is a continuation-in-part of application No. 14/834,185, filed on Aug. 24, 2015, now Pat. No. 9,765,027.

(60) Provisional application No. 62/040,886, filed on Aug. 22, 2014.

(51) Int. Cl.

| C07D 211/58 | (2006.01) |
| C07D 409/06 | (2006.01) |
| C07D 407/12 | (2006.01) |
| A61K 31/16 | (2006.01) |
| A61K 31/4465 | (2006.01) |
| A61K 31/451 | (2006.01) |
| C07D 405/12 | (2006.01) |
| C07D 409/12 | (2006.01) |
| A61K 31/4468 | (2006.01) |

(52) U.S. Cl.
CPC ............ *C07D 211/58* (2013.01); *A61K 31/16* (2013.01); *A61K 31/4465* (2013.01); *A61K 31/4468* (2013.01); *A61K 31/451* (2013.01); *C07D 405/12* (2013.01); *C07D 407/12* (2013.01); *C07D 409/06* (2013.01); *C07D 409/12* (2013.01)

(58) Field of Classification Search
CPC ................ A61K 31/16; A61K 31/4465; A61K 31/4468; A61K 31/451; A61P 25/00; C07D 211/58; C07D 405/12; C07D 407/12; C07D 409/06; C07D 409/12
See application file for complete search history.

(56) References Cited

U.S. PATENT DOCUMENTS

| 4,024,147 | A | * | 5/1977 | Archibald | ............ | C07D 211/58 546/194 |
| 5,214,055 | A | * | 5/1993 | Peglion | ................ | C07D 211/58 514/320 |
| 7,834,010 | B2 | * | 11/2010 | Klaveness | ................ | A61P 1/04 514/230.2 |
| 9,756,027 | B2 | * | 9/2017 | Li | ........................... | H04L 63/08 |
| 10,617,681 | B2 | * | 4/2020 | Vardanyan | ........... | C07D 409/12 |

* cited by examiner

*Primary Examiner* — Kara R McMillian

(74) *Attorney, Agent, or Firm* — Nguyen Tarbet LLC

(57) ABSTRACT

The present invention provides using a substituted 1-arylalkyl-4-acylaminopiperidine compound of Formula I:

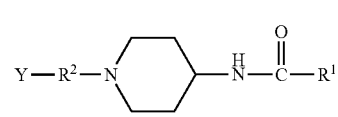

to treat various clinical conditions including, but not limited to, hemorrhagic shock, nicotine withdrawal symptoms, gastrointestinal side effects of opioids, cancer therapy, epithelial wounds, herpes zoster infection, or opioid-induced pruritus. In compound of Formula I, $R^1$ is $C_{1-10}$ alkyl, $C_{1-10}$ haloalkyl, optionally substituted aryl, or optionally substituted heteroaryl; $R^2$ is $C_{1-6}$ alkylene; Y is optionally substituted aryl, optionally substituted heteroaryl, or a moiety of the formula —C(=O)—$X^1$, wherein $X^1$ is —$OR^3$ or —$NR^4R^5$, where each of $R^3$, $R^4$ and $R^5$ is H or $C_{1-10}$ alkyl.

17 Claims, No Drawings

SUBSTITUTED 1-ARYLALKYL-4-ACYLAMINOPIPERIDINE COMPOUNDS AND METHODS OF PRODUCING AND USING THE SAME

CROSS-REFERENCE TO RELATED APPLICATIONS

This application is a continuation of Ser. No. 15/756,014, filed Feb. 27, 2018, which is a 35 U.S.C. § 371 U.S. National Stage Patent Application of PCT Patent Application No. PCT/US16/30649, filed May 4, 2016, which is a continuation-in-part Application of U.S. patent application Ser. No. 14/834,185, now U.S. Pat. No. 9,765,027, issued on Sep. 19, 2017, all of which are incorporated herein by reference in their entirety. This application is also a continuation-in-part Application of U.S. patent application Ser. No. 16/236,981, filed Dec. 31, 2018, which is divisional of U.S. patent application Ser. No. 15/709,394, filed Sep. 19, 2017, which is continuation-in-part of U.S. patent application Ser. No. 14/834,185, filed Aug. 24, 2015, now U.S. Pat. No. 9,765,027, issued Sep. 19, 2017, which claims the priority benefit of U.S. Provisional Application No. 62/040,886, filed Aug. 22, 2014, all of which are also incorporated herein by reference in their entirety.

STATEMENT REGARDING FEDERALLY FUNDED RESEARCH

This invention was made with government support under Grant Nos. P01 DA006284; R01 GM108040; and R01 DK017420 awarded by the National Institutes of Health. The government has certain rights in the invention.

FIELD OF THE INVENTION

The present invention relates to substituted 1-arylalkyl-4-acylaminopiperidine compounds and methods for producing and using the same to treat various clinical conditions. Exemplary clinical conditions that can be treated using the compounds of the invention include, but not limited to, hemorrhagic shock, nicotine withdrawal symptoms, gastrointestinal side effects of opioids, cancer therapy, epithelial wounds, herpes zoster infection, or opioid-induced pruritus.

BACKGROUND OF THE INVENTION

Opioid receptor antagonists (i.e., "opioid antagonists") are drugs that bind to the opioid receptors, typically with higher affinity than agonists. Unlike agonists, antagonists do not activate the receptors to which they bind. Thus, opioid antagonists are often used to block the receptor from the action of agonists to counteract life-threatening depression of the central nervous and respiratory systems. Accordingly, opioid antagonists are often used to treat opioid overdose and opioid dependency.

Opioid receptor antagonists modulate numerous central and peripheral effects including opioid abuse, the development of tolerance and dependence, and opioid-induced constipation, alcohol and cocaine abuse, depression, and immune responses. The diverse therapeutic applications of μ-opioid antagonists include opioid-overdose-induced respiratory depression, opioid and cocaine abuse, alcohol dependence, smoking cessation, obesity, psychosis and for therapies for dyskinesia associated with Parkinson's disease.

Commonly known opioid antagonists include naltrexone, naloxone and nalmefene which have therapeutic utility in a variety of conditions. Opioid antagonists effectively block the receptor from the action of both naturally occurring agonists (e.g., morphine, codeine, thebaine) and synthetic agonists (e.g., fentanyl, pethidine, levorphanol, methadone, tramadol, dextropropoxyphene) and uses include counteracting life-threatening depression of the central nervous and respiratory systems.

During the last two decades only Alvimopan, a peripherally acting μ-opioid antagonist for the treatment of postoperative ileus has been approved as new drug, and some azabicyclohexane derivatives and series of bi(hetero)aryl ethers as biological tools have been proposed as new chemical entities in this class of compounds.

In a commonly assigned PCT Patent Application No. PCT/US15/46585 and the corresponding U.S. patent application Ser. No. 14/834,185, both of which were filed on Aug. 24, 2015, and are incorporated herein by reference in their entirety, treatment of various clinical conditions using substituted 1-arylalkyl-4-acylaminopiperidine compounds are discussed, such as those associated with opioid abuse, the development of opioid tolerance and dependence, opioid-induced constipation, cocaine abuse, depression, and immune responses, opioid-overdose-induced respiratory depression, alcohol dependence, smoking cessation, obesity, psychosis, dyskinesia associated with Parkinson's disease, Raynaud's disease, hypertension, scleroderma, anxiety and panic disorders.

The present inventors have found that substituted 1-arylalkyl-4-acylaminopiperidine compounds are useful in treating other clinical conditions.

SUMMARY OF THE INVENTION

Some aspects of the invention are based on the discovery by the present inventors that substituted 1-arylalkyl-4-acylaminopiperidine compounds are useful in treating other clinical conditions, such as hemorrhagic shock, nicotine withdrawal symptoms, gastrointestinal side effects of opioids, cancer therapy, epithelial wounds, herpes zoster infection, opioid-induced pruritus as well as other clinical conditions. It is believed that because substituted 1-arylalkyl-4-acylaminopiperidine compounds of the invention have been shown to be effective antagonists of μ-, δ- and/or κ-opioid receptors and/or $α_2$-adrenoreceptor, compounds of the invention can be used to treat clinical condition that are due to activation of any one or more μ-, δ- and κ-opioid receptors and $α_2$-adrenoreceptor, in particular $α_{2B}$-adrenoreceptor.

In one particular aspect of the invention, the method of the invention is used to treat a clinical condition selected from the group consisting of hemorrhagic shock, nicotine withdrawal symptoms, gastrointestinal side effects of opioids, cancer therapy, epithelial wounds, herpes zoster infection, and opioid-induced pruritus. Such a method includes administering a therapeutically effective amount of a compound of Formula I to the subject in need of such a treatment:

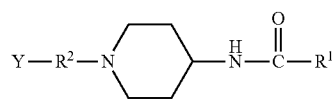

I where $R^1$ is $C_{1-10}$ alkyl, $C_{1-10}$ haloalkyl, optionally substituted aryl, or optionally substituted heteroaryl; $R^2$ is $C_{1-6}$ alkylene; Y is optionally substituted aryl, optionally substituted heteroaryl, or a moiety of the formula —C(=O)—X$^1$, wherein X$^1$ is —OR$^3$ or —NR$^4$R$^5$, where each of R$^3$, R$^4$ and R$^5$ is H or C$_{1-10}$ alkyl.

DETAILED DESCRIPTION OF THE INVENTION

Definitions: Unless the context requires otherwise, the following definitions are used.

"Alkyl" refers to a saturated linear monovalent hydrocarbon moiety or a saturated branched monovalent hydrocarbon moiety. Exemplary alkyl group include, but are not limited to, methyl, ethyl, n-propyl, 2-propyl, tert-butyl, pentyl, and the like.

"Alkylene" refers to a saturated linear saturated divalent hydrocarbon moiety or a branched saturated divalent hydrocarbon moiety. Exemplary alkylene groups include, but are not limited to, methylene, ethylene, propylene, butylene, iso-butylene, pentylene, and the like.

"Aryl" refers to a monovalent mono-, bi- or tricyclic aromatic hydrocarbon moiety of 6 to 15 ring atoms which is optionally substituted with one or more substituents. More specifically the term aryl includes, but is not limited to, phenyl, 1-naphthyl, and 2-naphthyl, and the derivatives thereof. When substituted, the aryl group typically contains one, two or three substituents within the ring structure. Moreover, when two or more substituents are present in an aryl group, each substituent is independently selected. Exemplary substituents for the aryl group include, but are not limited to, alkyl, haloalkyl, heteroalkyl, halo, nitro, cyano, optionally substituted phenyl, heteroaryl, haloalkoxy, —OR' (where R' is H, alkyl or a phenol protecting group) and carboxyl (i.e., a moiety of the formula —COX, where X is —OR$^a$ or —NR$^b$R$^c$, where each of R$^a$, R$^b$, R$^c$ is independently H, alkyl, or a corresponding protecting group.

"Aralkyl" refers to a moiety of the formula —R$^b$R$^c$ where R$^b$ is an alkylene group and R$^c$ is an optionally substituted aryl group as defined herein. Exemplary aralkyl groups include, but are not limited to, benzyl, phenylethyl, (halo-substituted phenyl)ethyl, and the like.

The terms "halo," "halogen" and "halide" are used interchangeably herein and refer to fluoro, chloro, bromo, or iodo.

"Haloalkyl" refers to an alkyl group as defined herein in which one or more hydrogen atom is replaced by same or different halo atoms. The term "haloalkyl" also includes perhalogenated alkyl groups in which all alkyl hydrogen atoms are replaced by halogen atoms. Exemplary haloalkyl groups include, but are not limited to, —CH$_2$Cl, —CF$_3$, —CH$_2$CF$_3$, —CH$_2$CCl$_3$, and the like.

The term "heteroaryl" means a monovalent monocyclic or bicyclic aromatic moiety of 5 to 12 ring atoms containing one, two, or three ring heteroatoms selected from N, O, or S, the remaining ring atoms being C. Exemplary heteroaryl includes, but is not limited to, pyridyl, furanyl, thiophenyl, thiazolyl, isothiazolyl, triazolyl, imidazolyl, isoxazolyl, pyrrolyl, pyrazolyl, pyrimidinyl, benzofuranyl, isobenzofuranyl, benzothiazolyl, benzoisothiazolyl, benzotriazolyl, indolyl, isoindolyl, benzoxazolyl, quinolyl, isoquinolyl, benzimidazolyl, benzisoxazolyl, benzothiophenyl, dibenzofuran, and benzodiazepin-2-one-5-yl, and the like. The heteroaryl ring can optionally be substituted with one or more substituents, typically one or two substituents. When two or more substituents are present in heteroaryl, each substituent is independently selected. Exemplary substituents for heteroaryl include, but are not limited to, substituents described for aryl group above.

"Pharmaceutically acceptable excipient" refers to an excipient that is useful in preparing a pharmaceutical composition that is generally safe, non-toxic and neither biologically nor otherwise undesirable, and includes excipient that is acceptable for veterinary use as well as human pharmaceutical use.

"Pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, oxalic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

The terms "pro-drug" and "prodrug" are used interchangeably herein and refer to any compound which releases an active parent drug according to Formula I in vivo when such prodrug is administered to a mammalian subject. Prodrugs of a compound of Formula I are prepared by modifying one or more functional group(s) present in the compound of Formula I in such a way that the modification(s) may be cleaved in vivo to release the parent compound. Prodrugs include compounds of Formula I wherein a hydroxy, amino, or sulfhydryl group in a compound of Formula I is bonded to any group that may be cleaved in vivo to regenerate the free hydroxyl, amino, or sulfhydryl group, respectively. Examples of prodrugs include, but are not limited to, esters (e.g., acetate, formate, and benzoate derivatives), carbamates (e.g., N,N-dimethylaminocarbonyl) of hydroxy functional groups in compounds of Formula I, and the like.

"Protecting group" refers to a moiety, except alkyl groups, that when attached to a reactive group in a molecule masks, reduces or prevents that reactivity. Examples of protecting groups can be found in T. W. Greene and P. G. M. Wuts, *Protective Groups in Organic Synthesis*, 3$^{rd}$ edition, John Wiley & Sons, New York, 1999, and Harrison and Harrison et al., *Compendium of Synthetic Organic Methods*, Vols. 1-8 (John Wiley and Sons, 1971-1996), which are incorporated herein by reference in their entirety. Representative hydroxy protecting groups include acyl groups, benzyl and trityl ethers, tetrahydropyranyl ethers, trialkylsilyl ethers and allyl ethers. Representative amino protecting groups include, formyl, acetyl, trifluoroacetyl, benzyl, benzyloxycarbonyl (CBZ), tert-butoxycarbonyl (Boc), trimethyl silyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC), and the like.

"Corresponding protecting group" means an appropriate protecting group corresponding to the heteroatom (i.e., N, O, P or S) to which it is attached.

"A therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

"Treating" or "treatment" of a disease includes: (1) preventing the disease, i.e., causing the clinical symptoms of the disease not to develop in a mammal that may be exposed to or predisposed to the disease but does not yet experience or display symptoms of the disease; (2) inhibiting the disease, i.e., arresting or reducing the development of the disease or its clinical symptoms; or (3) relieving the disease, i.e., causing regression of the disease or its clinical symptoms.

As used herein, the term "treating", "contacting" or "reacting" refers to adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

As used herein, the terms "those defined above" and "those defined herein" when referring to a variable incorporates by reference the broad definition of the variable as well as narrower definitions, if any.

Compounds of the Invention: Some aspects of the invention provide N-substituted piperidin-4-yl compounds of Formula I:

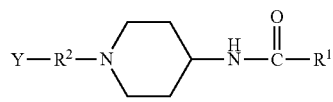

I where $R^1$ is $C_{1-10}$ alkyl, $C_{1-10}$ haloalkyl, optionally substituted aryl, or optionally substituted heteroaryl; $R^2$ is $C_{1-6}$ alkylene; Y is optionally substituted aryl, optionally substituted heteroaryl, or a moiety of the formula —C(=O)—$X^1$, wherein $X^1$ is —$OR^3$ or —$NR^4R^5$, where each of $R^3$, $R^4$ and $R^5$ is H or $C_{1-10}$ alkyl. In some aspects of the invention, when $R^1$ is optionally substituted aryl, then Y is a substituted heteroaryl, or a moiety of the formula —C(=O)—$X^1$. Still in another aspect of the invention, when Y is heteroaryl or aryl, then $R^1$ is $C_{1-10}$ alkyl, $C_{1-10}$ haloalkyl, or optionally substituted heteroaryl.

Yet still in another aspect of the invention, compounds of invention are those of Formula I as broadly disclosed above provided when Y is heteroaryl, $R^1$ is not optionally substituted phenyl, in particular $R^1$ is not phenyl.

Still in another aspect of the invention, compounds of invention are those of Formula I as broadly disclosed above provided when Y is phenyl, $R^1$ is not substituted phenyl.

In some embodiments, $R^1$ is selected from the group consisting of $C_{1-8}$ alkyl, $C_{1-8}$ haloalkyl, optionally substituted phenyl, and optionally substituted furyl. In some instances, R1 is selected from the group consisting of ethyl, 7-bromoheptyl, fur-2-yl, fur-3-yl, and phenyl.

Yet in other embodiments, $R^2$ is $C_{1-4}$ alkylene. In one particular embodiment, $R^2$ is ethylene.

Still in other embodiments, Y is selected from the group consisting of optionally substituted phenyl, optionally substituted furyl, optionally substituted thiophenyl and a moiety of the formula —C(=O)—$X^1$, where $X^1$ is those defined herein. Within these embodiments, in some instances Y is selected from the group consisting of phenyl, thiophenyl (typically thiophen-2-yl), and a moiety of the formula —C(=O)—$OR^3$, where $R^3$ is $C_{1-10}$ alkyl.

Still further, combinations of the various embodiments of different variables described herein form other embodiments. For example, in one particularly preferred embodiment $R^1$ is ethyl, $R^2$ is ethylene, Y is phenyl. In this manner, a variety of specific compounds are embodied within the present invention including, but not limited to, N-(1-phenethylpiperidin-4-yl)propionamide ("HCV-3"), methyl 3-(4-propionamidopiperidin-1-yl)propanoate, N-(1-phenethylpiperidin-4-yl)furan-2-carboxamide, N-(1-phenethylpiperidin-4-yl)furan-3-carboxamide, N-(1-(2-(thiophen-2-yl)ethyl)piperidin-4-yl)propionamide, 8-bromo-N-(1-phenethylpiperidin-4-yl)octanamide, and N-(1-phenethylpiperidin-4-yl)benzamide.

Utility: The compounds of the invention have a variety of physiological properties. In particular, the present inventors have discovered that compounds of the invention can modulate a variety of receptors including, but not limited to, μ-, δ-, and κ-opioid receptors and $α_2$-adrenoreceptor, in particular $α_{2B}$-adrenoreceptor. In particular, the compounds of the invention are found to be antagonists of these receptors. Accordingly, any clinical conditions that are due or associated with at least in part to abnormal activation of one or more of these receptors can be treated by the compounds of the invention.

In some embodiments, compounds of the invention are found to be opioid antagonists. As such, compounds of the invention bind to the opioid receptors with higher affinity than opioid agonists but do not activate the opioid receptors. Thus, compounds of the invention can be used to effectively block the receptor from the action of both naturally occurring opioid agonists (e.g., morphine, codeine, thebaine) and synthetic opioid agonists (e.g., fentanyl, pethidine, levorphanol, methadone, tramadol, dextropropoxyphene). Accordingly, compounds of the invention can be used in a variety of clinical conditions associated with opioid use including, but not limited to, counteracting life-threatening depression of the central nervous and respiratory systems. Therefore, compounds of the invention can be used for emergency overdose and dependence treatment.

Compounds of the invention can modulate numerous central and peripheral effects including those associated with opioid abuse, the development of opioid tolerance and dependence, opioid-induced constipation, alcohol and cocaine abuse, depression, and immune responses. The diverse therapeutic applications of compounds of the invention include opioid-overdose-induced respiratory depression, opioid and cocaine abuse, alcohol dependence, smoking cessation, obesity, psychosis and for the treatment of dyskinesia associated with Parkinson's disease.

In another aspect of the invention, the present inventors have discovered that compounds of the invention are antagonists of adrenoreceptors. Thus, compounds of the invention bind to the adrenoreceptors and inhibit the action of these receptors. α-Adrenoreceptor antagonists (commonly known as α-blockers) may selectively bind to the $α_1$-adrenoreceptors or the $\alpha_2$-adrenoreceptors, or they may bind non-selectively to both adrenoreceptor types. In some embodiments, compounds of the invention are found to be selective $\alpha_{2B}$-adrenoreceptor antagonists. As used herein, the term "selective $\alpha_{2B}$-adrenoreceptor antagonist" means that the ratio of binding to $\alpha_{2B}$-adrenoreceptor compared to other adrenoreceptor is at great than 1:1, typically, at least about 1.5:1, often at least about 2:1, more often at least about 5:1, and most often at least about 10:1. Compounds of the invention can be used to treat various clinical conditions that are related to or associated with abnormal activation of adrenoreceptors including, but not limited to, Raynaud's disease, hypertension, scleroderma, anxiety and panic disorders, and in the treatment of dyskinesia associated with Parkinson's disease.

Utility for compounds of various receptor antagonists are known. See, for example, Singleton et al., Cancer, 2015, 121(16), 2681-2688 (use of μ-opioid receptor antagonists in cancer treatment); Jackson et al., Neuropharmacology, 2015, 97, 270-274 (use of κ-opioid receptor antagonist for nicotine withdrawal); Bear et al., U.S. Pat. Appl. Publication No. US 20150202199 A1 (treatments for depression and other diseases using dopaminergic agents); Noble et al., British Journal of Pharmacology, 2015, 172(16), 3964-3979 (opioid receptor antagonists for drug abuse and/or the prevention of relapse treatment); Brokjaer et al., Neurogastroenterology & Motility, 2015, 27(5), 693-704 (opioid antagonists for treatment of gastrointestinal side effects such as pain); Labuzek et al., Pharmacological Reports, 2014, 66(5), 811-820 (opioid antagonists for pharmacotherapy for gambling disorder); Soyka et al., Current Drug Abuse Reviews, 2008, 1(3), 280-291 (opioid antagonists for pharmacological treatment of alcohol dependence); Nutt et al., Psychopharmacology, (London, United Kingdom), 2014, 28(1), 8-22 (treatment of alcohol dependence); Tek et al., Journal of Clinical Psychopharmacology, 2014, 34(5), 608-612 (use of opioid antagonists in arresting antipsychotic-associated weight gain); Shi et al., Guoji Yaoxue Yanjiu Zazhi, 2013, 40(4), 439-442 (combinations of opioid agonists and opioid antagonists to treat side effects of opioid agonists and decrease risk of drug abuse); Wang et al., Expert Opinion on Investigational Drugs, 2013, 22(10), 1225-1227 (use of opioid antagonists for treatment of opioid-induced constipation); Taylor et al., Expert Opinion on Investigational Drugs, 2013, 22(4), 517-525 (use of opioid antagonists as analgesics); Zagon et al., PCT patent application publication number WO 2013016480 A1 (use of opioid antagonists for treatment of epithelial wounds); Pisak et al., PCT Patent Application Publication No. WO 2012134410 A1 (use of opioid antagonists for treating scleroderma including systemic sclerosis); Hopp et al., PCT Patent Application Publication No. WO 2012089738 A1 (use of a combination of opioid agonists and opioid antagonists for the treatment of Parkinson's disease and associated symptoms); Tenhola et al., J. Endocrinological Investigation, 2012, 35(2), 227-230 (effect of opioid antagonists on sex hormone secretion, e.g., using an opioid antagonists to increase the secretion of GnRH in the hypothalamus which then causes a pulsatile release of LH in the pituitary and secretion of testosterone); Miller et al., Amer. J. Health-System Pharmacy, 2011, 68(15), 1419-1425 (use of opioid antagonists for management of opioid-induced pruritus); Toledano et al., U.S. Pat. Appl. Publ. No. 20110269727 A1 (using opioid antagonists and direct-acting $\alpha_2$-adrenergic agonists to reduce allodynic back pain); Pisak et al., PCT Patent Application Publication No. WO 2011123084 A1 (using an opioid receptor antagonist to treat herpes zoster disease); Ockert et al., J. Addiction Med., 2011, 5(2), 110-114 (using an opioid antagonist for outpatient opioid detoxification and/or the treatment of opioid withdrawal); Moss et al., U.S. Pat. Appl. Publ. No. 20100286059 A1 (use of opioid antagonists for inhibiting or reducing, cellular proliferation and migration, such as endothelial cell proliferation and migration, including that associated with angiogenesis, as well as attenuating cancerous tumor growth and metastasis); Zagon et al., U.S. Pat. Appl. Publ. No. US 20100273821 A1 (using opioid antagonists to treat dry eye); Lobmaier et al., Eur. J. Clin. Pharm., 2010, 66(6), 537-545 (use of the opioid antagonists for the treatment of intoxication and overdose); Stotts et al., Expert Opinion on Pharmacotherapy, 2009, 10(11), 1727-1740 (using opioid antagonists for treating opioid dependency); Hopp et al., PCT Patent Application Publication No. WO 2010003963 A1 (using opioid antagonists for treating urinary retention); and Hayward et al., PCT Patent Application Publication No. WO 2009156889 A1 (using opioid antagonists for treating obesity, obesity-related co-morbidities, and CNS disorders). Accordingly, compounds of the invention can be used treat all of these clinical conditions. In addition, compounds of the invention can be used in the treatment of various forms of depression and/or mood disorders, including, for example, breakthrough depression and treatment-refractory depression, and other mood disorders.

Some of the more specific exemplary clinical conditions that can be treated by compounds of the invention include, but are not limited to, hemorrhagic shock, nicotine withdrawal symptoms, gastrointestinal side effects of opioids, cancer therapy, epithelial wounds, herpes zoster infection, and opioid-induced pruritus.

Administration and Pharmaceutical Composition: The present invention includes pharmaceutical compositions comprising at least one compound of the invention or a pharmaceutically acceptable salt or solvate thereof, together with at least one pharmaceutically acceptable carrier, and optionally other therapeutic and/or prophylactic ingredients.

In general, the compounds of the invention are administered in a therapeutically effective amount by any of the accepted modes of administration for agents that serve similar utilities. Suitable dosage ranges are typically 1-500 mg daily, typically 1-100 mg daily, and often 1-30 mg daily, depending on numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases is typically able, without undue experimentation and in reliance upon personal knowledge and the disclosure of this application, to ascertain a therapeutically effective amount of the compounds of the invention.

Typically, compounds of the invention are administered as pharmaceutical formulations including those suitable for oral (including buccal and sub-lingual), rectal, nasal, topical, pulmonary, vaginal, or parenteral (including intramuscular, intraarterial, intrathecal, subcutaneous and intravenous) administration or in a form suitable for administration by inhalation or insufflation. Typical manner of administration is generally oral using a convenient daily dosage regimen which can be adjusted according to the degree of affliction.

A compound or compounds of the invention, together with one or more conventional adjuvants, carriers, or diluents, can be placed into the form of pharmaceutical compositions and unit dosages. The pharmaceutical compositions and unit dosage forms can be comprised of conventional ingredients in conventional proportions, with or without additional active compounds or principles, and the unit dosage forms can contain any suitable effective amount of the active ingredient commensurate with the intended daily dosage range to be employed. The pharmaceutical compositions can be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. Formulations containing about one (1) milligram of active ingredient or, more broadly, about 0.01 to about one hundred (100) milligrams, per tablet, are accordingly suitable representative unit dosage forms.

The compounds of the invention can be formulated in a wide variety of oral administration dosage forms. The pharmaceutical compositions and dosage forms can comprise a compound or compounds of the invention or pharmaceutically acceptable salts thereof as the active component. The pharmaceutically acceptable carriers can be either solid or liquid. Solid form preparations include powders, tablets, pills, capsules, cachets, suppositories, and dispersible granules. A solid carrier can be one or more substances which can also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. The powders and tablets preferably contain from about one (1) to about seventy (70) percent of the active compound. Suitable carriers include but are not limited to magnesium carbonate, magnesium stearate, talc, sugar, lactose, pectin, dextrin, starch, gelatine, tragacanth, methylcellulose, sodium carboxymethylcellulose, a low melting wax, cocoa butter, and the like. The term "preparation" is intended to include the formulation of the active compound with encapsulating material as carrier, providing a capsule in which the active component, with or without carriers, is surrounded by a carrier, which is in association with it. Similarly, cachets and lozenges are included. Tablets, powders, capsules, pills, cachets, and lozenges can be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions can be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizers, and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and can contain, in addition to the active component, colorants, flavors, stabilizers, buffers, artificial and natural sweeteners, dispersants, thickeners, solubilizing agents, and the like.

The compounds of the invention can also be formulated for parenteral administration (e.g., by injection, for example bolus injection or continuous infusion) and can be presented in unit dose form in ampoules, pre-filled syringes, small volume infusion or in multi-dose containers with an added preservative. The compositions can take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and can contain formulatory agents such as preserving, wetting, emulsifying or suspending, stabilizing and/or dispersing agents. Alternatively, the active ingredient can be in powder form, obtained by aseptic isolation of sterile solid or by lyophilization from solution for constitution before use with a suitable vehicle, e.g., sterile, pyrogen-free water.

The compounds of the invention can be formulated for topical administration to the epidermis as ointments, creams or lotions, or as a transdermal patch. Ointments and creams can, for example, be formulated with an aqueous or oily base with the addition of suitable thickening and/or gelling agents. Lotions can be formulated with an aqueous or oily base and will in general also contain one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatine and glycerine or sucrose and acacia; and mouthwashes comprising the active ingredient in a suitable liquid carrier.

The compounds of the invention can be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the invention can also be formulated for vaginal administration. Pessaries, tampons, creams, gels, pastes, foams or sprays containing in addition to the active ingredient such carriers as are known in the art to be appropriate.

The compounds of the invention can be formulated for nasal administration. The solutions or suspensions are applied directly to the nasal cavity by conventional means, for example, with a dropper, pipette or spray. The formulations can be provided in a single or multidose form. In the latter case of a dropper or pipette, this can be achieved by the patient administering an appropriate, predetermined volume of the solution or suspension. In the case of a spray, this can be achieved for example by means of a metering atomizing spray pump.

The compounds of the invention can be formulated for aerosol administration, particularly to the respiratory tract and including intranasal administration. The compound will generally have a small particle size for example of the order of five (5) microns or less. Such a particle size can be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol can conveniently also contain a surfactant such as lecithin. The dose of drug can be controlled by a metered valve. Alternatively the active ingredients can be provided in a form of a dry powder, for example, a powder mix of the compound in a suitable powder base such as lactose, starch, starch derivatives such as hydroxypropylmethyl cellulose and polyvinylpyrrolidine (PVP). The powder carrier typically forms a gel in the nasal cavity. The powder composition can be presented in unit dose form, for example, in capsules or cartridges of e.g., gelatine or blister packs from which the powder can be administered by means of an inhaler.

When desired, formulations can be prepared with enteric coatings adapted for sustained or controlled release administration of the active ingredient. For example, the compounds of the invention can be formulated in transdermal or subcutaneous drug delivery devices. These delivery systems are advantageous when sustained release of the compound is necessary or desired and when patient compliance with a treatment regimen is crucial. Compounds in transdermal delivery systems are frequently attached to a skin-adhesive solid support. The compound of interest can also be combined with a penetration enhancer, e.g., Azone (1-dodecylazacycloheptan-2-one). Sustained release delivery systems can be inserted subcutaneously into the subdermal layer by surgery or injection. The subdermal implants encapsulate the compound in a lipid soluble membrane, e.g., silicone rubber, or a biodegradable polymer, e.g., polylactic acid.

The pharmaceutical preparations are typically in unit dosage forms. In such form, the preparation is often subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Other suitable pharmaceutical carriers and their formulations are described in Remington: *The Science and Practice of Pharmacy* 1995, edited by E. W. Martin, Mack Publishing Company, 19th edition, Easton, Pa.

When it is possible that, for use in therapy, therapeutically effective amounts of a compound of Formula I, as well as pharmaceutically acceptable salts thereof, can be administered as the raw chemical, it is possible to present the active ingredient as a pharmaceutical composition. Accordingly, the disclosure further provides pharmaceutical compositions, which include therapeutically effective mounts of compounds of Formula I or pharmaceutically acceptable salts thereof or a prodrug thereof, and one or more pharmaceutically acceptable carriers, diluents, or excipients. When applied to a combination, the term refers to combined amounts of the active ingredients that result in the therapeutic effect, whether administered in combination, serially, or simultaneously. The compounds of Formula I and pharmaceutically acceptable salts thereof, are as described above. The carrier(s), diluent(s), or excipient(s) must be acceptable in the sense of being compatible with the other ingredients of the formulation and not deleterious to the recipient thereof. In accordance with another aspect of the disclosure there is also provided a process for the preparation of a pharmaceutical formulation including admixing a compound of Formula I, or a pharmaceutically acceptable salt thereof or a prodrug thereof, with one or more pharmaceutically acceptable carriers, diluents, or excipients.

When the compositions of this disclosure comprise a combination of a compound of the present disclosure and one or more additional therapeutic or prophylactic agent, both the compound and the additional agent are usually present at dosage levels of between about 10 to 150%, and more typically between about 10 and 80% of the dosage normally administered in a monotherapy regimen.

Additional objects, advantages, and novel features of this invention will become apparent to those skilled in the art upon examination of the following examples thereof, which are not intended to be limiting. In the Examples, procedures that are constructively reduced to practice are described in the present tense, and procedures that have been carried out in the laboratory are set forth in the past tense.

EXAMPLES

Synthesis of 1-Phenethylpiperidin-4-one oxime: 1-Phenethylpiperidin-4-one 10.15 g (0.05 mol) dissolved in 60 mL of ethanol was added dropwise at 0° C. to a water solution of hydroxylamine in water (prepared by adding 13.8 g (0.1 mol) of $K_2CO_3$ to the solution of 6.95 g (0.1 mol) hydroxylamine hydrochloride in 50 mL of water). The mixture was left overnight. Ethanol was evaporated under slight vacuum. Water was added and the mixture was stirred on ice bath for an hour. The separated solid product was filtered, washed with water and dried on the air. The crude oxime 10.71 g (98.25%), m.p. 132-134° C. was used in the next reaction without further purification. MS (ESI): 219.1 (MH+).

Synthesis of 1-Phenethylpiperidin-4-amine: 1-Phenethylpiperidin-4-one oxime 6.54 g (0.03 mol) was dissolved in 100 ml of dry i-AmOH on heating and ten fold excess of sodium 6.9 g (0.3 mol) was slowly added to the stirred solution in small pieces, keeping temperature around 110° C. Solution was stirred at 110° C. for two hours and left to cool to room temperature. The mixture was diluted with 150 ml of ether followed by 75 mL. Organic layer was separated, dried over $MgSO_4$, and filtered. Solvent was removed and the product was distilled under vacuum to give 4.3 g (70%) of 1-phenethylpiperidin-4-amine. B.P. 138-142° C./1.5 mm. MS (ESI): 205. (MH+).

Synthesis of N-(1-Phenethylpiperidin-4-yl)propionamide: Propionyl chloride 2.775 g (0.03 mol) in 5.55 mL of $CHCl_3$ was added dropwise to a cooled (0° C.) solution of 4.08 g (0.02 mol) 1-phenethylpiperidin-4-amine and 3.03 g (0.03 mol) of $Et_3N$ in 30 mL of $CHCl_3$. The mixture was allowed to reach room temperature and stirred overnight. After work-up with 5% aqueous solution of $NaHCO_3$, organic layer was separated, washed with water, dried over $MgSO_4$, and filtered. Filtrate was concentrated and crystallized from hexane to give 4.9 g (94%) of N-(1-phenethylpiperidin-4-yl)propionamide. M.p. 134-135° C. MS (ESI): 261.2 (MH+). $^1H$ NMR (600 MHz, $CDCl_3$): δ 7.27 (t, J=7.4 Hz, 2H), 7.19 (m, 3H), 5.32 (d, J=7.4 Hz, 1H), 3.82 (qt, J=7.8, 4.2 Hz, 1H), 2.92 (dt, J=11.8, 3.4 Hz, 2H), 2.79 (m*, 2H), 2.59 (m*, 2H), 2.19 (q, J=7.5 Hz, 2H), 2.18 (m, 2H), 1.95 (dtd, J=12.4, 4.4, 1.7 Hz, 2H), 1.46 (qd, J=11.7, 3.8 Hz, 2H), 1.15 (t, J=7.5 Hz, 3H). $^{13}C$ NMR (150 MHz, $CDCl_3$): δ 173.0, 140.2, 128.6, 128.4, 126.0, 60.4, 52.3, 46.3, 33.7, 32.3, 29.8, 9.9.

Synthesis of N-(1-Phenethylpiperidin-4-yl)propionamide oxalate. Oxalic acid 1 g (0.011 mol) in 10 mL of ethanol was added dropwise to the solution of 2.93 g (0.011 mol) of N-(1-phenethylpiperidin-4-yl)propionamide in 29.3 mL of ethanol. The mixture was left overnight. Obtained crystals were separated and dried in dessicator over $P_2O_5$ to give 3.5 g of N-(1-phenethylpiperidin-4-yl)propionamide oxalate. M.P. 216-218° C. MS (ESI): 261.2 (M+). X-ray crystallography data for a representative compound of the invention, N-(1-phenethyl-piperidin-4-yl)propionamide oxalate confirmed the structure.

Synthesis of N-(1-phenethylpiperidin-4-yl)furan-2-carboxamide. 2-Furoyl chloride 0.827 g, (0.00636 mol) dissolved in 0.25 mL of dry dichloromethane was added dropwise to a cooled (0° C.) solution of 1.08 g (0.00468 mol) 1-phenethylpiperidin-4-amine and 0.178 mL of $Et_3N$ in 2 mL of $CHCl_3$. The mixture was allowed to reach room temperature and stirred overnight. After work-up with 5% solution of $NaHCO_3$, organic layer was separated, washed with water, dried over $MgSO_4$, and filtered. Filtrated was concentrated to yield a white solid. The product was washed with hexanes to obtain an analytically pure sample. Yield: 0.0845 g (58.3%). MS (ESI): 299.3 (MH+). $^1$H NMR (400 MHz, $CDCl_3$): δ 1.63 (d, J=11.93 Hz, 2H), 2.05 (d, J=12.33 Hz, 2H), 2.26 (t, J=11.35, 11.35 Hz, 2H), 2.64 (dd, J=6.16, 10.21 Hz, 2H), 2.83 (dd, J=6.12, 10.24 Hz, 2H), 2.99 (d, J=12.01 Hz, 2H), 3.98 (m, 1H), 6.21 (d, J=8.20 Hz, 1H), 6.49 (dd, J=1.79, 3.47 Hz, 1H), 7.10 (dd, J=0.84, 3.47 Hz, 1H), 7.24 (m, 5H), 7.43 (dd, 0.84, 1.77 Hz, 1H). $^{13}$C NMR (100 MHz, $CDCl_3$): δ 32.67, 34.17, 46.27, 46.61, 52.76, 60.88, 112.60, 114.57, 126.56, 128.87, 129.13, 140.58, 144.16, 148.48, 158.13. Obtained compound was transformed to oxalate salt as described above.

Synthesis of N-(1-phenethylpiperidin-4-yl)furan-3-carboxamide. A solution of 3-furoyl chloride 0.827 g, (0.00636 mol) in 0.25 mL of dry dichloromethane was added dropwise to a mixture of cooled (0° C.) solution of 1.08 g (0.00468 mol) 1-phenethyl-piperidin-4-amine and 0.178 mL of $Et_3N$ in 2 mL of $CHCl_3$. The mixture was left to reach room temperature and stirred overnight. After work-up with 5% solution of $NaHCO_3$, organic layer was separated, washed with water, dried over $MgSO_4$, and filtered. Filtrate was concentrated to yield a white solid. The product was washed with hexanes to obtain an analytically pure sample. Yield: 0.104 g (72%). MS (ESI): 299.3 (MH+). $^1$H NMR (400 MHz, $CDCl_3$): δ 1.63 (m, 2H), 2.06 (d, J=11.35 Hz, 2H), 2.26 (m, J=11.35, 2H), 2.65 (m, 2H), 2.84 (m, 2H), 3.02 (d, J=11.86 Hz, 2H), 3.99 (m, 1H), 5.65 (d, J=7.99 Hz, 1H), 6.59 (dd, J=0.91, 1.93 Hz, 1H), 7.24 (m, 5H), 7.42 (dd, 1.58, 1.91 Hz, 1H), 7.91 (dd, J=0.90, 1.59 Hz, 1H). $^{13}$C NMR (100 MHz, $CDCl_3$): δ 32.04, 33.49, 46.43, 52.35, 60.26, 108.25, 122.66, 126.19, 128.46, 128.68, 139.88, 143.72, 144.69, 161.95. Obtained compound was transformed to oxalate salt as described above.

Synthesis of N-(1-phenethylpiperidin-4-yl)benzamide. A solution of benzoyl chloride 0.89 g, (0.00636 mol) in 0.25 mL of dry dichloromethane was added dropwise to a cooled (0° C.) solution of 1.08 g (0.00468 mol) 1-phenethylpiperidin-4-amine and 0.178 mL of $Et_3N$ in 2 mL of $CHCl_3$. The mixture was allowed to reach to room temperature and stirred for a night. After work-up with 5% solution of $NaHCO_3$, organic layer was separated, washed with water, dried over $MgSO_4$, and filtered. Concentration of the filtrate gave a white solid. The product was washed with hexanes to obtain an analytically pure sample. Yield: 0.132 g (87%). MS (ESI): 309.2 (MH+). $^1$H NMR (400 MHz, $CDCl_3$): δ 1.35 (t, J=7.29, 7.29 Hz, 2H), 1.64 (qd, J=3.80, 11.29, 11.29, 11.35 Hz, 2H), 2.08 (m, 2H), 2.27 (td, J=2.57, 11.61, 11.65 Hz, 2H), 2.64 (m, 2H), 2.83 (m, 2H), 3.00 (m, 3H), 4.04 (dddd, J=4.28, 8.29, 10.85, 15.24 Hz, 1H), 6.04 (d, J=7.94 Hz, 1H), 7.25 (m, 5H), 7.44 (m, 3H), 7.75 (m, 2H). $^{13}$C NMR (100 MHz, $CDCl_3$): δ 32.22, 33.71, 45.83, 46.97, 52.38, 60.42, 114.25, 126.12, 126.86, 128.42, 128.56, 128.68, 131.42, 134.75, 140.11, 166.88. Obtained compound was transformed to oxalate salt as described above.

Synthesis of 8-Bromo-N-(1-phenethylpiperidin-4-yl)octanamide: A solution of 1-phenethylpiperidin-4-amine (0.101 g, 0.00493 mol), 8-bromooctanoic acid (0.1 g, 0.00448 mol), HATU (0.170 g, 0.00448 mol), HOAt (0.061 g, 0.00448 mol), and DIEPA (0.314 mL, 0.0018 mol) in dry DMF was stirred at room temperature overnight. The reaction mixture was then quenched with 0.5 M $KHSO_4$ solution followed by the addition of dichloromethane. The organic and aqueous layers were separated, and the aqueous layer was extracted with dichloromethane (3×5 mL) followed by washing with $NaHCO_3$ solution and brine. The organic extracts were combined, dried over anhydrous magnesium sulfate, and filtered. Concentration of the filtrate gave a white solid. Yield: 0.146 g (80%). MS (ESI): 409.2 (MH+). $^1$H NMR (400 MHz, $CDCl_3$): δ 1.32-2.34 (m, 14H), 2.82-3.01 (m, 11H), 3.16 (dd, J=6.53, 10.91 Hz, 1H), 3.49 (d, J=11.91 Hz, 1H), 4.63 (dt, J=5.61, 5.61, 8.76 Hz, 1H), 7.24 (m, 4H), 7.42 (dd, J=4.46, 8.37, 1H), 8.02 (m, 1H). $^{13}$C NMR (100 MHz, $CDCl_3$): δ 25.17, 25.45, 27.85, 28.70, 28.75, 31.46, 36.55, 38.61, 81.47, 120.73, 128.66, 128.86, 129.19, 151.29, 162.71, 173.62. Obtained compound was transformed to oxalate salt as described above.

Synthesis of 1-Benzylpiperidin-4-one oxime: A solution of 1-benzylpiperidin-4-one (28.35 g, 0.15 mol) in 60 mL of EtOH was added to the cooled to 0° C. solution of hydroxylamine hydrochloride (20.85 g, 0.30 mol) in 75 mL of $H_2O$. To the resulting mixture was added a solution of $K_2CO_3$ (20.7 g, 0.15 mol) in 75 mL of $H_2O$. The reaction mixture was then allowed to reach room temperature and stirred overnight. The EtOH was removed and the reaction mixture was cooled in an ice bath to allow the product to crystallize out of solution. The product was filtered and washed several times with $H_2O$ and recrystallized in EtOH. Yield: 27.78 g (70.17%).

Synthesis of 1-Benzylpiperidin-4-amine: Na metal (6.9 g, 0.3 mol) was added to a 110° C. solution of 1-benzylpiperidin-4-one oxime (6.12 g, 0.03 mol) in 90 mL of iso-amyl alcohol. The reaction mixture was allowed to cool to room temperature and stirred until the reaction mixture became a thick slurry. The slurry was dissolved in 50 mL of diethyl ether and 25 mL of $H_2O$. The organic layer was separated, washed with $H_2O$, dried over anhydrous magnesium sulfate, and filtered. The filtrate was concentrated to yield a yellow oil. The crude product was purified via column chromatography using silica gel and a DCM:MeOH solvent in a ratio of 4:1 with an additional 1% of $Et_3N$. Yield: 3.7 g (64%).

Synthesis of N-(1-Benzylpiperidin-4-yl)propionamide. To a 0° C. solution of 1-benzylpiperidin-4-amine (3.7 g, 0.019 mol) and 5 mL of $Et_3N$ (0.05 mol) in 45 mL of dry dichloromethane was added a solution of propionyl chloride (2.17 mL, 0.025 mol) in 10 mL of dichloromethane. The reaction mixture was allowed to reach room temperature and stirred overnight. To the reaction mixture was added 4 mL of $NH_4OH$ and 45 mL of $H_2O$. The aqueous layer was separated and extracted with dichloromethane. The combined organic layers were washed with $NaHCO_3$ solution and brine, dried over anhydrous magnesium sulfate, filtered and concentrated to yield a white solid. The product was washed with hexanes to obtain an analytically pure sample. Yield: 2.8 g (72%)

Synthesis of N-(Piperidin-4-yl)propionamide: A solution of N-(1-benzylpiperidin-4-yl)propionamide (0.7 g, 0.003 mol) in 30 mL of EtOH was hydrogenated for 24 hours under 50 psi of $H_2$ in the presence of 10% Pd/C (0.07 g) and 20% $Pd(OH)_2$ (0.07 g). The solution was filtered through celite and the solvent was evaporated to yield 0.467 g (99%) of the product.

Synthesis of methyl 3-(4-propionamidopiperidin-1-yl) propanoate. A solution of N-(piperidin-4-yl)propionamide (0.1 g, 0.0052 mol) in 2 mL of dry acetonitrile and methyl acrylate (0.071 mL, 0.00789 mol) was refluxed overnight. The solvent was removed and the crude product was purified by washing with hexanes to yield 0.90 g (71%) of the product. MS (ESI): 243.3 (MH+). $^1$H NMR (400 MHz, CDCl$_3$): δ 1.14 (t, J=7.59, 7.59 Hz, 3H), 1.41 (dtd, J=3.70, 11.10, 11.13, 12.61 Hz, 2H), 1.91 (m, 2H), 2.17 (m, 4H), 2.49 (m, 2H), 2.68 (m, 2H), 2.81 (m, 2H), 3.67 (s, 3H), 3.78 (dddd, J=4.29, 4.36, 11.92, 15.26, 1H), 5.25 (d, J=7.96 Hz, 1H). $^{13}$C NMR (100 MHz, CDCl$_3$): δ 10.02, 29.99, 32.41, 46.40, 51.76, 52.25, 55.63, 173.14, 174.05. Obtained compound was transformed to oxalate salt as described above.

Synthesis of N-(1-(2-(Thiophen-2-yl)ethyl)piperidin-4-yl)propionamide. A solution of N-(piperidin-4-yl)propionamide (0.1 g, 0.0064 mol), 2-(thiophen-2-yl)ethyl methanesulfonate (0.145 g, 0.704 mol), K$_2$CO$_3$ (0.097 g, 0.00704 mol), KI (0.032 g, 0.00192 mol), Et$_3$N (0.178 mL, 0.00128 mol) in 5 mL of dry acetonitrile was stirred overnight under refluxing conditions. The mixture was concentrated, and the residue was diluted with H$_2$O and extracted with ethyl acetate. The organic extracts were combined, dried over anhydrous magnesium sulfate, filtered and concentrated. The crude product was washed with hexanes to obtain an analytically pure sample. Yield: 0.101 g (60%). MS (ESI): 267.7 (MH+). $^1$H NMR (400 MHz, CDCl$_3$) δ 1.15 (t, J=7.58, 7.58 Hz, 3H), 1.47 (m, 2H), 1.95 (m, 2H), 2.18 (m, 4H), 2.64 (dd, J=6.87, 8.62 Hz, 2H), 2.90 (m, 2H), 3.00 (m, 2H), 3.82 (dddd, J=4.20, 8.31, 10.86, 15.17 Hz, 1H), 5.32 (d, J=7.95 Hz, 1H), 6.81 (dq, J=1.02, 1.02, 1.02, 3.20 Hz, 1H), 6.91 (dd, J=3.39, 5.14 Hz, 1H), 7.11 (dd, J=1.21, 5.13 Hz, 1H). $^{13}$C NMR (100 MHz, CDCl$_3$) δ 10.04, 28.06, 30.03, 32.15, 46.52, 52.42, 59.98, 123.62, 124.71, 126.69, 142.87, 173.15. Obtained compound was transformed to oxalate salt as described above.

Bioavailability and Stability: Compounds of the invention were studied in detail, using several parameters to evaluate bioavailability and stability. In summary, HCV-3 was highly bioavailable, indicating that it is likely that this compound is highly bioavailable when given by the oral route of administration.

Toxicity: The compound HCV-3 was studied for its toxicity in many animal models. HCV-3 showed virtually no toxicity even at high concentrations.

In vivo test: Compound HCV-3 showed significant inhibition of L-DOPA induced dyskinesias in both the Rodent and Primate in vivo models. HCV-3 was significantly more effective than amantadine which is the gold standard therapy for patients with Parkinson's disease to reduce the effects of L-dopa-induced dyskinesia.

Cytochrome P450 Inhibition: The objective was to access the potential of HCV3 to inhibit the main cytochrome P450 isoforms, CYP1A2, CYP2B6, CYP2C8, CYP2C9, CYP2C19, CYP2D6 and CYP3A4 (2 substrates). HCV3 (0.1 μM-25 μM) was incubated with human liver microsomes and NADPH in the presence of a cytochrome P450 isoform-specific probe substrate. The metabolites were monitored by mass spectrometry. A decrease in the formation of the metabolite compared to the vehicle control is used to calculate an IC$_{50}$ value for each P450 (concentration of HCV3 which produces 50% inhibition).

CYP1A2 Inhibition: Six test compound concentrations (0.1, 0.25, 1, 2.5, 10, 25 μM in DMSO; final DMSO concentration 0.3%) were incubated with human liver microsomes (0.25 mg/mL) and NADPH (1 mM) in the presence of the probe substrate phenacetin (30 μM) for 5 min at 37° C. The selective CYP1A2 inhibitor, α-naphthoflavone, was screened alongside HCV3 as a positive control.

CYP2B6 Inhibition: Six test compound concentrations (0.1, 0.25, 1, 2.5, 10, 25 μM in DMSO; final DMSO concentration 0.3%) were incubated with human liver microsomes (0.1 mg/mL) and NADPH (1 mM) in the presence of the probe substrate bupropion (110 μM) for 5 min at 37° C. The selective CYP2B6 inhibitor, ticlopidine, was screened alongside HCV3 as a positive control.

CYP2C8 Inhibition: Six test compound concentrations (0.1, 0.25, 1, 2.5, 10, 25 μM in DMSO; final DMSO concentration 0.3%) were incubated with human liver microsomes (0.25 mg/mL) and NADPH (1 mM) in the presence of the probe substrate paclitaxel (7.5 μM) for 30 min at 37° C. The selective CYP2C8 inhibitor, montelukast, was screened alongside HCV3 as a positive control.

CYP2C9 Inhibition: Six test compound concentrations (0.1, 0.25, 1, 2.5, 10, 25 μM in DMSO; final DMSO concentration 0.25%) were incubated with human liver microsomes (1 mg/mL) and NADPH (1 mM) in the presence of the probe substrate tolbutamide (120 μM) for 60 min at 37° C. The selective CYP2C9 inhibitor, sulphaphenazole, was screened alongside HCV3 as a positive control.

CYP2C19 Inhibition: Six test compound concentrations (0.1, 0.25, 1, 2.5, 10, 25 μM in DMSO; final DMSO concentration 0.25%) were incubated with human liver microsomes (0.5 mg/mL) and NADPH (1 mM) in the presence of the probe substrate mephenytoin (25 μM) for 60 min at 37° C. The selective CYP2C19 inhibitor, tranylcypromine, was screened alongside HCV3 as a positive control.

CYP2D6 Inhibition: Six test compound concentrations (0.1, 0.25, 1, 2.5, 10, 25 μM in DMSO; final DMSO concentration 0.25%) were incubated with human liver microsomes (0.5 mg/mL) and NADPH (1 mM) in the presence of the probe substrate dextromethorphan (5 μM) for 5 min at 37° C. The selective CYP2D6 inhibitor, quinidine, was screened alongside HCV3 as a positive control.

CYP3A4 Inhibition (Midazolam): Six test compound concentrations (0.1, 0.25, 1, 2.5, 10, 25 μM in DMSO; final DMSO concentration 0.26%) were incubated with human liver microsomes (0.1 mg/mL) and NADPH (1 mM) in the presence of the probe substrate midazolam (2.5 μM) for 5 min at 37° C. The selective CYP3A4 inhibitor, ketoconazole, was screened alongside HCV3 as a positive control.

CYP3A4 Inhibition (Testosterone): Six test compound concentrations (0.1, 0.25, 1, 2.5, 10, 25 μM in DMSO; final DMSO concentration 0.275%) were incubated with human liver microsomes (0.5 mg/mL) and NADPH (1 mM) in the presence of the probe substrate testosterone (50 μM) for 5 min at 37° C. The selective CYP3A4 inhibitor, ketoconazole, was screened alongside HCV3 as a positive control.

The reactions were terminated by methanol. The samples were then centrifuged and the supernatants were analyzed for acetaminophen, hydroxybupropion, 6α-hydroxypaclitaxel 4-hydroxytolbutamide, 4-hydroxymephenytoin, dextrorphan, 1-hydroxymidazolam and 6ß-hydroxytestosterone by LC-MS/MS. Formic acid in deionized water (final concentration 0.1%) containing internal standard is added to the final sample prior to analysis. A decrease in the formation of the metabolites compared to vehicle control was used to calculate an IC$_{50}$ value (concentration of HCV3 which produces 50% inhibition).

Results: Out of the 7 CYPs tested, HCV3 was only found to significantly inhibit CYP2D6, and weakly CYP2C19. With CYP2C19, the inhibition was too weak to generate an IC$_{50}$ value, and 36.4% inhibition was observed at the top concentration of 25 micromolar. With CYP2D6, an IC$_{50}$ of 4.2 micromolar was obtained. No significant inhibition was observed at CYP2B6, CYP2C9, CYP3A4 (with either substrate), CYP2C8 or CYP1A2.

hERG Channel Inhibition ($IC_{50}$ Determination): Mammalian cells expressing the hERG potassium channel were dispensed into 384-well planar arrays and hERG tail-currents measured by whole-cell voltage-clamping. A range of concentrations of the test compound was then added to the cells and a second recording of the hERG current was made. The percent change in hERG current was calculated and used to calculate an $IC_{50}$ value (test compound concentration which produces 50% inhibition).

The experiments were performed on an IonWorks™ automated patch clamp instrument (Molecular Devices LLC), which simultaneously performs electrophysiology measurements for 48 single cells in a specialized 384-well plate (PatchPlate™). All cell suspensions, buffers and test compound solutions were at room temperature during the experiment. The cells used were Chinese hamster ovary (CHO) cells stably transfected with hERG (cell-line obtained from Cytomyx, UK). A single-cell suspension was prepared in extracellular solution (Dulbecco's phosphate buffered saline with calcium and magnesium pH 7.2) and aliquots were added automatically to each well of a PatchPlate™. The cells were then positioned over a small hole at the bottom of each well by applying a vacuum beneath the plate to form an electrical seal. The vacuum was applied through a single compartment common to all wells which was filled with intracellular solution (buffered to pH 7.2 with HEPES). The resistance of each seal was measured via a common ground-electrode in the intracellular compartment and individual electrodes placed into each of the upper wells.

Electrical access to the cell was then achieved by circulating a perforating agent, amphotericin B, underneath the PatchPlate™. The pre-compound hERG current was then measured. An electrode was positioned in the extracellular compartment and a holding potential of −80 mV applied for 15 sec. The hERG channels were then activated by applying a depolarizing step to +40 mV for 5 sec and then clamped at −50 mV for 4 sec to elicit the hERG tail current, before returning to −80 mV for 0.3 sec. Compound dilutions were prepared by diluting a DMSO solution (default 10 mM) of the test compound using a factor 5 dilution scheme into DMSO, followed by dilution into extracellular buffer such that the final concentrations tested were typically 0.008, 0.04, 0.2, 1, 5, 25 µM (final DMSO concentration 0.25%). The IonWorks™ instrument automatically added test compound dilutions to the upper wells of the PatchPlate™. The test compound was left in contact with the cells for 300 sec before recording currents using the same voltage-step protocol as in the pre-compound scan. Quinidine, an established hERG inhibitor, was included as a positive control, and vehicle control (0.25% DMSO) as negative control.

Each concentration is tested in 4 replicate wells on the PatchPlate™ (maximum of 32 data points). Filters were applied to ensure only acceptable cells were used to assess hERG inhibition.

Results: Over the concentration range tested (up to 25 micromolar) no dose-response was obtained, therefore the inhibition IC50 is >25 micromolar. There was a hint of some inhibition at the top concentration of 25 micromolar, with 32.5% inhibition observed (insufficient to generate an IC50 value). The results showed the compound had weak or no significant hERG inhibition activity.

MDR1-MDCK Permeability and Identification of P-gp Substrate (Bi-directional): Madin-Darby canine kidney (MDCK) cells are an epithelial cell line of canine kidney origin. These cells can be stably transfected to express active P-glycoprotein (MDR1-MDCK) and are ideal for studying drug efflux. Test compound was added to either the apical or basolateral side of a confluent monolayer of MDR1-MDCK cells and permeability was measured by monitoring the appearance of the test compound on the opposite side of the monolayer using LC-MS/MS. The efflux ratio (ER) was calculated from the ratio of B-A and A-B permeabilities. Experiments were performed in the absence and presence of a P-glycoprotein (P-gp) inhibitor (cyclosporin A (10 µM)) to determine whether the compound was subject to P-gp mediated efflux.

Experimental Procedure: MDR1-MDCK cells obtained from the NIH (Rockville, Md., USA) were used between passage numbers 6-30. Cells were seeded onto Millipore Multiscreen Transwell plates at $3.4 \times 10^5$ cells/cm². The cells were cultured in DMEM and media was changed on day 3. On day 4 the permeability study was performed. Cell culture and assay incubations were carried out at 37° C. in an atmosphere of 5% $CO_2$ with a relative humidity of 95%. On the day of the assay, the monolayers were prepared by rinsing both apical and basolateral surfaces twice with Hanks Balanced Salt Solution (HBSS) at the desired pH warmed to 37° C. Cells were then incubated with HBSS at the desired pH in both apical and basolateral compartments for 40 min to stabilize physiological parameters.

The dosing solutions were prepared by diluting test compound with assay buffer to give a final test compound concentration of 10 µM (final DMSO concentration of 1% v/v). The fluorescent integrity marker lucifer yellow was also included in the dosing solution. Where applicable, the P-gp inhibitor was also included. Analytical standards were prepared from test compound DMSO dilutions and transferred to buffer, maintaining a 1% v/v DMSO concentration. Test compound permeability was measured on two occasions, in the absence and in the presence of a P-gp inhibitor on both sides of the monolayer. The assay buffer was composed of supplemented HBSS pH 7.4.

For assessment of A-B permeability, HBSS was removed from the apical compartment and replaced with test compound dosing solution. The apical compartment insert was then placed into a companion plate containing fresh buffer (containing 1% v/v DMSO or, where applicable, a P-gp inhibitor, maintaining a 1% v/v DMSO concentration). For assessment of B-A permeability, HBSS was removed from the companion plate and replaced with test compound dosing solution. Fresh buffer (containing 1% v/v DMSO or, where applicable, a P-gp inhibitor, maintaining a 1% v/v DMSO concentration) was added to the apical compartment insert, which was then placed into the companion plate. At 60 min the apical compartment inserts and the companion plates were separated and apical and basolateral samples diluted for analysis. Test compound permeability was assessed in duplicate. Compounds of known permeability characteristics were run as controls on each assay plate. Test and control compounds were quantified by LC-MS/MS cassette analysis using an 8-point calibration with appropriate dilution of the samples. Cyprotex generic analytical conditions were used. The starting concentration ($C_0$) was determined from the dosing solution and the experimental recovery calculated from $C_0$ and both apical and basolateral compartment concentrations.

The integrity of the monolayer throughout the experiment was checked by monitoring lucifer yellow permeation using fluorimetric analysis. Lucifer yellow permeation was high if monolayers have been damaged. If a lucifer yellow $P_{app}$ value was above a pre-defined threshold in one individual test compound well, the compound was re-tested or an n=1 result was reported. If lucifer yellow $P_{app}$ values were above the threshold in both replicate wells for a test compound, the compound was re-tested. If this re-occurred upon repeat in both wells then toxicity or inherent fluorescence of the test compound was assumed. No further experiments were performed in this instance.

Results: HCV3 was highly permeable in the MDCK assay. There was a slight difference between the plus and minus inhibitor data in terms of the efflux ratio obtained (1.48 minus inhibitor, versus 0.929 plus inhibitor). Typically, a ratio of greater than 2 is indicative that efflux is occurring. The control compounds behaved as expected, with prazosin (a P-gp substrate) showing efflux in the absence of Cyclosporin A, which was inhibited in its presence.

Cytochrome P450 Induction (Cryopreserved Hepatocytes, mRNA Assessment): Experiments were conducted to assess the potential of HCV3 to induce the cytochrome P450 isoforms CYP1A2, CYP2B6 and CYP3A4 using an mRNA endpoint in cryopreserved hepatocytes.

Experimental Procedure: Cryopreserved human hepatocytes from a single donor were seeded on a 96-well collagen coated plate so that the final seeding density is $0.1 \times 10^6$ cells/well (final volume per well 0.1 mL). The cells were then incubated in seeding medium at 37° C., 95% humidity, 5% $CO_2$ to allow the cells to attach. After 4 hr, the seeding medium was replaced with 0.1 mL of pre-warmed serum-free Williams E medium (William's E containing 100 IU/mL penicillin, 100 µg/mL streptomycin, 10 µg/mL insulin, 2 mM L-glutamine and 0.1 µM hydrocortisone). The next day, cells were dosed with test compound in assay medium (six final test compound concentrations between 100 µM and 0.4 µM; final DMSO concentration 0.1%). Positive control inducers, omeprazole (100 µM) for CYP1A2, phenobarbital (1000 µM) for CYP2B6 and rifampicin (25 µM) for CYP3A4, were incubated alongside the test compound. Negative control wells were included where the test compound is replaced by vehicle solvent (typically 0.1% DMSO in assay medium). Each test or control compound was dosed in triplicate at each concentration. The cells were exposed to the solutions for 72 hr with fresh solution added every 24 hr.

For mRNA assessment, all media was removed from each of the wells and the cells were washed once with 0.1 mL of pre-warmed assay medium. The cells were lysed by adding 100 µL of lysis buffer to each well. Total RNA was then isolated from the hepatocyte lysates. Reverse transcription was performed and quantitative PCR analysis was performed on the resulting cDNA, using gene-specific primer probe sets for CYP1A2, CYP2B6 and CYP3A4 target cDNA and endogenous control. Samples were analyzed using an ABI 7900 HT real time PCR system.

Data Analysis: For mRNA assessment, relative fold mRNA expression was determined based on the threshold cycle ($C_T$) data of target gene relative to endogenous control for each reaction, and normalized to negative control using the $2^{-\Delta\Delta C_T}$ method. To determine the statistical significance of any fold change of mRNA expression, a one way ANOVA with two tailed Dunnett's post-test was performed using the $\Delta C_T$ values. Differences with a p value less than 0.05 were taken to be significant.

Results: To summarize, HCV-3 didn't cause a statistically significant change in CYP1A2 or CYP3A4 mRNA expression at any concentration tested. At 100 µM a slight, yet statistically significant decrease in mRNA expression with CYP2B6 was observed. Therefore, no CYP induction was observed, but potentially some down-regulation of CYP2B6 at the highest concentration tested. The positive and negative control compounds included alongside HCV-3 responded as expected.

Caco-2 Permeability (A-B or Bi-directional): Caco-2 cells were used as an in vitro model of the human intestinal epithelium and permit assessment of the intestinal permeability of potential drugs.

Experimental Procedure: Caco-2 cells obtained from the ATCC were used between passage numbers 40-60. Cells were seeded onto Millipore Multiscreen Transwell plates at $1 \times 10^5$ cells/cm$^2$. The cells were cultured in DMEM and media was changed every two or three days. On day 20 the permeability study was performed. Cell culture and assay incubations were carried out at 37° C. in an atmosphere of 5% $CO_2$ with a relative humidity of 95%. On the day of the assay, the monolayers were prepared by rinsing both apical and basolateral surfaces twice with Hanks Balanced Salt Solution (HBSS) at the desired pH warmed to 37° C. Cells were then incubated with HBSS at the desired pH in both apical and basolateral compartments for 40 min to stabilize physiological parameters. The dosing solutions were prepared by diluting test compound with assay buffer to give a final test compound concentration of 10 µM (final DMSO concentration of 1% v/v). The fluorescent integrity marker lucifer yellow was also included in the dosing solution. Analytical standards were prepared from test compound DMSO dilutions and transferred to buffer, maintaining a 1% v/v DMSO concentration.

For assessment of A-B permeability, HBSS was removed from the apical compartment and replaced with test compound dosing solution. The apical compartment insert was then placed into a companion plate containing fresh buffer (containing 1% v/v DMSO). For assessment of B-A permeability, HBSS was removed from the companion plate and replaced with test compound dosing solution. Fresh buffer (containing 1% v/v DMSO) was added to the apical compartment insert, which as then placed into the companion plate. At 120 min the apical compartment inserts and the companion plates were separated and apical and basolateral samples diluted for analysis.

Test compound permeability was assessed in duplicate. Compounds of known permeability characteristics were run as controls on each assay plate. Test and control compounds were quantified by LC-MS/MS cassette analysis using an 8-point calibration with appropriate dilution of the samples. Cyprotex generic analytical conditions were used. The starting concentration ($C_0$) was determined from the dosing solution and the experimental recovery calculated from $C_0$ and both apical and basolateral compartment concentrations. The integrity of the monolayer throughout the experiment was checked by monitoring lucifer yellow permeation using fluorimetric analysis. Lucifer yellow permeation is high if monolayers have been damaged. If a lucifer yellow $P_{app}$ value was above a pre-defined threshold in one individual test compound well, the compound was re-tested or an n=1 result was reported. If lucifer yellow $P_{app}$ values were above the threshold in both replicate wells for a test compound, the compound was re-tested. If this re-occurred upon repeat in both wells then toxicity or inherent fluorescence of the test compound was assumed. No further experiments were performed in this instance.

Results: The compound was highly permeable in both directions in the Caco-2 assay with an efflux ratio of 2.70. Without being bound by any theory, this is likely due to the compound carrying a basic functionality and is highly unlikely to indicate active transport. The assay has been run with a pH gradient (pH 6.8/7.4) to mimic the intestinal pH.

Time Dependent Inhibition of CYP2D6 (Dextromethorphan; $IC_{50}$ Shift): Six test compound concentrations (0.1, 0.25, 1, 2.5, 10, 25 µM; final DMSO concentration 0.25%, final microsome concentration 0.5 mg/mL) were either pre-incubated for 30 min in the absence and presence of NADPH or undergo a 0 min pre-incubation. The probe substrate dextromethorphan (5 µM) and NADPH (1 mM) were then added (final DMSO concentration 0.3%) and the samples incubated for 5 min at 37° C. The selective time dependent CYP2D6 inhibitor, paroxetine, was screened alongside the test compounds as a positive control. The reactions were terminated by the addition of an aliquot of the incubation into methanol. The samples were centrifuged at 2500 rpm for 30 min at 4° C., and aliquots of the supernatant are diluted with formic acid in deionised water (final concentration 0.1%) containing internal standard prior to analysis of dextrorphan by LC-MS/MS.

Results: The CYP time-dependent inhibition data was weaker than previously observed. In this assay the $IC_{50}$ was likely to be just over 25 µM, as approximately 40% inhibition was observed at this concentration (the 0 minute incubation). In the 30 minute plus NADPH incubation (the condition where we would expect to see time-dependent mechanism based inhibition) the percentage inhibition was the same, again at approximately 40%. As such, there is no evidence of time-dependent CYP2D6 inhibition with this compound.

Brain Tissue Binding: Experiments were conducted to measure the extent to which a compound binds to rat or mouse brain homogenate. Solutions of test compound (5 µM, 0.5% final DMSO concentration) were prepared in species specific brain homogenate (1 in 9 dilution in buffer) and in buffer. The experiment was performed using equilibrium dialysis with the two compartments separated by a semi-permeable membrane. The buffer solution was added to one side of the membrane and the brain homogenate solution to the other side. The system was allowed to reach equilibrium over 2 hr at 37° C. Standards were prepared in brain homogenate and buffer and were incubated at 37° C. during the equilibration period. After equilibration, samples were taken from both sides of the membrane. The solutions for each batch of compounds were combined into two groups (buffer and brain homogenate) then cassette analyzed by LC-MS/MS using two sets of calibration standards for buffer (7 points) and brain homogenate solutions (6 points). Cyprotex generic LC-MS/MS conditions ere used. Samples were quantified using standard curves prepared in the equivalent matrix. The compounds were tested in duplicate. Diazepam is included as a control compound in each experiment.

Results: The compound showed weak, or no noticeable binding to plasma proteins and there were very small species differences. In mouse no binding at all could be detected, therefore the fraction unbound could not be determined. In rat brain homogenate low binding was observed, with an fraction unbound of 0.249 reported. Therefore, the compound has a preference for binding brain tissue over plasma proteins.

In Vitro Pharmacology Binding Assays: Representative compounds were tested to determine $IC_{50}$ or $EC_{50}$ in receptor functional assays. One or more of the procedures disclosed in the following references were used: Devedjian, J. C. et al., *Eur. J. Pharmacol.*, 1994, 252, 43-49; Wang, J. B. et al., *FEBS Lett.*, 1994, 338, 217-222; Simonin, F. et al., *Mol. Pharmacol.*, 1994, 46, 1015-1021; Meng, F. et al., *Proc. Natl. Acad. Sci. U.S.A.*, 1993, 90, 9954-9958; Avidor-Reiss, T. et al., *FEBS Lett.*, 1995, 361, 70-74; Eason, M. G. et al., *J. Biol. Chem.*, 1992, 267, 15795-15801; Law, P. Y. et al., *Mol. Pharmacol.*, 1993, 43, 684-693. In each experiment and if applicable, the respective reference compound was tested concurrently with the test compounds. Compound binding was calculated as a % inhibition of the binding of a radioactively labeled ligand specific for each target. Cellular agonist effect was calculated as a % of control response to a known reference agonist for each target and cellular antagonist effect was calculated as a % inhibition of control reference agonist response for each target. Only the calculable IC50 and EC50 are reported below.

Methyl 3-(4-propionamidopiperidin-1-yl)propanoate

| Assay | $IC_{50}$ | $K_i$ | $EC_{50}$ | nH |
|---|---|---|---|---|
| $\alpha_{2B}$ (h) (antagonist radioligand) | 2.6E−04M | 1.8E−04M | | 1 |
| κ (KOP) (agonist radioligand) | 4.0E−04M | 2.7E−04M | | 0.8 |
| µ (MOP) (h) (agonist effect) | | | 2.9E−04M | |
| µ (MOP) (h) (agonist radioligand) | 2.0E−04M | 8.2E−05M | | 0.5 |

N-(1-phenethylpiperidin-4-yl)furan-2-carboxamide

| Assay | $IC_{50}$ | $K_i$ | $K_B$ | $EC_{50}$ | nH |
|---|---|---|---|---|---|
| $\alpha_{2B}$ (h) (antagonist effect) | 3.8E−04M | | 5.0E−05M | | |
| $\alpha_{2B}$ (h) (antagonist radioligand) | 4.6E−06M | 3.0E−06M | | | 0.7 |
| $\delta_2$ (DOP) (antagonist effect) | 1.4E−05M | | 2.4E−06M | | |
| $\delta_2$ (DOP) (h) (agonist | 9.7E−05M | 5.8E−05M | | | 1 |
| κ (KOP) (agonist effect) | | | | 5.6E−04M | |
| κ (KOP) (agonist radioligand) | 1.8E−05M | 1.2E−05M | | | 1.1 |
| µ (MOP) (h) (agonist radioligand) | 2.6E−07M | 1.1E−07M | | | 0.8 |
| µ (MOP) (h) (antagonist effect) | 1.4E−05M | | 1.5E−06M | | |

N-(1-phenethylpiperidin-4-yl)furan-3-carboxamide

| Assay | $IC_{50}$ | $K_i$ | $K_B$ | $EC_{50}$ | nH |
|---|---|---|---|---|---|
| $\alpha_{2B}$ (h) (antagonist effect) | 2.3E−04M | | 5.0E−05M | | |
| $\alpha_{2B}$ (h) (antagonist radioligand) | 3.0E−06M | 3.0E−06M | | | 0.7 |
| $\delta_2$ (DOP) (antagonist effect) | 1.5E−05M | | 2.4E−06M | | |

-continued

| Assay | IC$_{50}$ | K$_i$ | K$_B$ | EC$_{50}$ | nH |
|---|---|---|---|---|---|
| δ$_2$ (DOP) (h) (agonist radioligand) | 4.1E−05M | 5.8E−05M | | | 1 |
| κ (KOP) (agonist effect) | | | | 5.6E−04M | |
| κ (KOP) (agonist radioligand) | 8.4E−06M | 1.2E−05M | | | 1.1 |
| μ (MOP) (h) (agonist radioligand) | 4.8E−07M | 1.1E−07M | | | 0.8 |
| μ (MOP) (h) (antagonist effect) | 3.1E−05M | | 1.5E−06M | | |

8-bromo-N-(1-phenethylpiperidin-4-yl)octanamide

| Assay | IC$_{50}$ | K$_i$ | K$_B$ | EC$_{50}$ | nH |
|---|---|---|---|---|---|
| α$_{2B}$ (h) (antagonist effect) | 3.6E−04M | | 4.6E−05M | | |
| α$_{2B}$ (h) (antagonist radioligand) | 5.7E−06M | 3.8E−06M | | | 0.8 |
| κ (KOP) (agonist radioligand) | 6.0E−05M | 4.0E−05M | | | 0.5 |
| μ (MOP) (h) (agonist radioligand) | | | | 8.0E−04 M | |
| μ (MOP) (h) (antagonist effect) | 9.5E−05M | 3.9E−05M | | | 0.4 |

N-(1-phenethylpiperidin-4-yl)benzamide

| Assay | IC$_{50}$ | K$_i$ | K$_B$ | EC$_{50}$ | nH |
|---|---|---|---|---|---|
| α$_{2B}$(h) (antagonist effect) | 3.5E−04M | | 4.6E−05M | | |
| α$_{2B}$(h) (antagonist radioligand) | 4.0E−06M | .27E−06M | | | 1.3 |
| δ$_2$ (DOP) (antagonist effect) | 9.6E−05M | | 1.7E−06M | | |
| δ$_2$ (DOP) (h) (agonist radioligand) | 8.7E−05M | 5.1E−05M | | | 0.7 |
| κ (KOP) (agonist effect) | | | | 4.6E−04M | |
| κ (KOP) (agonist radioligand) | 3.2E−05M | 2.1E−05M | | | 0.6 |
| μ (MOP) (h) (agonist radioligand) | 2.5E−06M | 1.0E−06M | | | 0.9 |
| μ (MOP) (h) (antagonist effect) | 3.8E−05M | | 4.1E−06M | | |

N-(1-(2-(thiophen-2-yl)ethyl)piperidin-4-yl)propionamide

| Assay | IC$_{50}$ | K$_i$ | K$_B$ | EC$_{50}$ | nH |
|---|---|---|---|---|---|
| α$_{2B}$ (h) (antagonist effect) | 4.4E−04M | | 5.7E−05M | | |
| α$_{2B}$ (h) (antagonist radioligand) | 1.1E−05M | 7.6E−06M | | | 1.2 |
| δ$_2$ (DOP) (h) (agonist radioligand) | 4.1E−04M | 2.5E−04M | | | 0.9 |
| κ (KOP) (agonist effect) | | | | 3.1E−04M | |
| κ (KOP) (agonist radioligand) | 1.6E−05M | 1.1E−05M | | | 0.6 |
| μ (MOP) (h) (agonist radioligand) | | | | 6.6E−06M | |
| μ (MOP) (h) (antagonist effect) | 9.0E−07M | 3.7E−07M | | | 0.6 |

Results showing an inhibition (or stimulation for assays run in basal conditions) higher than 50% are considered to represent significant effects of the test compounds. Results showing an inhibition (or stimulation) between 25% and 50% are indicative of weak to moderate effects. Results showing an inhibition (or stimulation) lower than 25% are not considered significant. High negative values (≥50%) that are sometimes obtained with high concentrations of test compounds are generally attributable to nonspecific effects of the test compounds in the assays. On rare occasion they could suggest an allosteric effect of the test compound The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter. All references cited herein are incorporated by reference in their entirety.

What is claimed is:

1. A method for treating a clinical condition selected from the group consisting of dyskinesia associated with Parkinson's Disease, hemorrhagic shock, nicotine withdrawal symptoms, gastrointestinal side effects of opioids, cancer therapy side effects, epithelial wounds, herpes zoster infection, and opioid-induced pruritus, said method comprising administering a therapeutically effective amount of an $\alpha_{2B}$ adrenoreceptor antagonist to a patient in need of such a treatment, wherein said $\alpha_{2B}$ adrenoreceptor antagonist is of the formula:

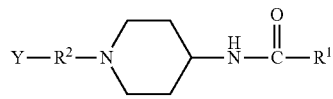

wherein
$R^1$ is $C_{1-10}$ alkyl, $C_{1-10}$ haloalkyl, optionally substituted aryl, or optionally substituted heteroaryl;
$R^2$ is $C_{1-6}$ alkylene;
Y is optionally substituted aryl, optionally substituted heteroaryl, or a moiety of the formula —C(=O)$X^1$, wherein $X^1$ is —OR$^3$ or —NR$^4$R$^5$, where each of $R^3$, $R^4$ and $R^5$ is H or $C_{1-10}$ alkyl.

2. The method of claim 1, wherein $R^1$ is selected from the group consisting of ethyl, 7-bromoheptyl, fur-2-yl, fur-3-yl, and phenyl.

3. The method of claim 1, wherein $R^2$ is ethylene.

4. The method of claim 1, wherein Y is selected from the group consisting of phenyl, thiophen-2-yl, and a moiety of the formula —C(=O)—OR$^3$, where $R^3$ is $C_{1-10}$ alkyl.

5. The method of claim 1, wherein said $\alpha_{2B}$ adrenoreceptor antagonist compound is selected from the group consisting of N-(1-phenethylpiperidin-4-yl)propionamide, methyl 3-(4-propionamidopiperidin-1-yl)propanoate, N-(1-phenethylpiperidin-4-yl)furan-2-carboxamide, N-(1-phenethylpiperidin-4-yl)furan-3-carboxamide, N-(1-(2-(thiophen-2-yl)ethyl)piperidin-4-yl)propionamide, 8-bromo-N-(1-phenethylpiperidin-4-yl)octanamide, and N-(1-phenethylpiperidin-4-yl)benzamide.

6. A method for treating dyskinesia associated with Parkinson's Disease, hemorrhagic shock, nicotine withdrawal symptoms, gastrointestinal side effects of opioids, cancer therapy side effects, epithelial wounds, herpes zoster infection, or opioid-induced pruritus in a subject, said method comprising administering a therapeutically effective amount of an N-substituted piperidin-4-yl compound to a subject in need of such a treatment, wherein said N-substituted piperidin-4-yl compound is of the Formula:

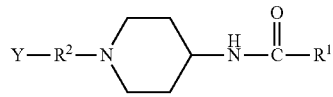

wherein
$R^1$ is $C_{1-10}$ alkyl, $C_{1-10}$ haloalkyl, optionally substituted aryl, or optionally substituted heteroaryl;
$R^2$ is $C_{1-6}$ alkylene;
Y is optionally substituted aryl, optionally substituted heteroaryl, or a moiety of the formula —C(=O)—$X^1$, wherein $X^1$ is —OR$^3$ or —NR$^4$R$^5$, where each of $R^3$, $R^4$ and $R^5$ is H or $C_{1-10}$ alkyl.

7. The method of claim 6, wherein $R^1$ is selected from the group consisting of ethyl, 7-bromoheptyl, fur-2-yl, fur-3-yl, and phenyl.

8. The method of claim 6, wherein $R^2$ is ethylene.

9. The method of claim 6, wherein Y is selected from the group consisting of phenyl, thiophen-2-yl, and a moiety of the formula —C(=O)—OR$^3$, where $R^3$ is $C_{1-10}$ alkyl.

10. The method of claim 6, wherein said $\alpha_{2B}$ adrenoreceptor antagonist compound is selected from the group consisting of N-(1-phenethylpiperidin-4-yl)propionamide, methyl 3-(4-propionamidopiperidin-1-yl)propanoate, N-(1-phenethylpiperidin-4-yl)furan-2-carboxamide, N-(1-phenethylpiperidin-4-yl)furan-3-carboxamide, N-(1-(2-(thiophen-2-yl)ethyl)piperidin-4-yl)propionamide, 8-bromo-N-(1-phenethylpiperidin-4-yl)octanamide, and N-(1-phenethylpiperidin-4-yl)benzamide.

11. The method of claim 6, wherein said method comprises treating dyskinesia associated with Parkinson's disease.

12. A method for treating a clinical condition selected from the group consisting of dyskinesia associated with Parkinson's Disease, nicotine withdrawal symptoms, gastrointestinal side effects of opioids, side-effects of cancer therapy, and opioid-induced pruritus in a subject, said method comprising administering a therapeutically effective amount of an N-substituted piperidin-4-yl compound to a subject in need of such a treatment, wherein said N-substituted piperidin-4-yl compound is of the Formula:

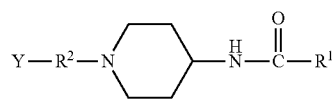

wherein
$R^1$ is $C_{1-10}$ alkyl, $C_{1-10}$ haloalkyl, optionally substituted aryl, or optionally substituted heteroaryl;
$R^2$ is $C_{1-6}$ alkylene;
Y is optionally substituted aryl, optionally substituted heteroaryl, or a moiety of the formula —C(=O)—$X^1$, wherein $X^1$ is —OR$^3$ or —NR$^4$R$^5$, where each of $R^3$, $R^4$ and $R^5$ is H or $C_{1-10}$ alkyl.

13. The method of claim 12, wherein $R^1$ is selected from the group consisting of ethyl, 7-bromoheptyl, fur-2-yl, fur-3-yl, and phenyl.

14. The method of claim 12, wherein $R^2$ is ethylene.

15. The method of claim 12, wherein Y is selected from the group consisting of phenyl, thiophen-2-yl, and a moiety of the formula —C(=O)—OR$^3$, where $R^3$ is $C_{1-10}$ alkyl.

16. The method of claim 12, wherein said $\alpha_{2B}$ adrenoreceptor antagonist compound is selected from the group consisting of N-(1-phenethylpiperidin-4-yl)propionamide, methyl 3-(4-propionamidopiperidin-1-yl)propanoate, N-(1-phenethylpiperidin-4-yl)furan-2-carboxamide, N-(1-phenethylpiperidin-4-yl)furan-3-carboxamide, N-(1-(2-(thiophen-2-yl)ethyl)piperidin-4-yl)propionamide, 8-bromo-N-(1-phenethylpiperidin-4-yl)octanamide, and N-(1-phenethylpiperidin-4-yl)benzamide.

17. The method of claim 12, wherein said method comprises treating dyskinesia associated with Parkinson's disease.

* * * * *